Figure 1:
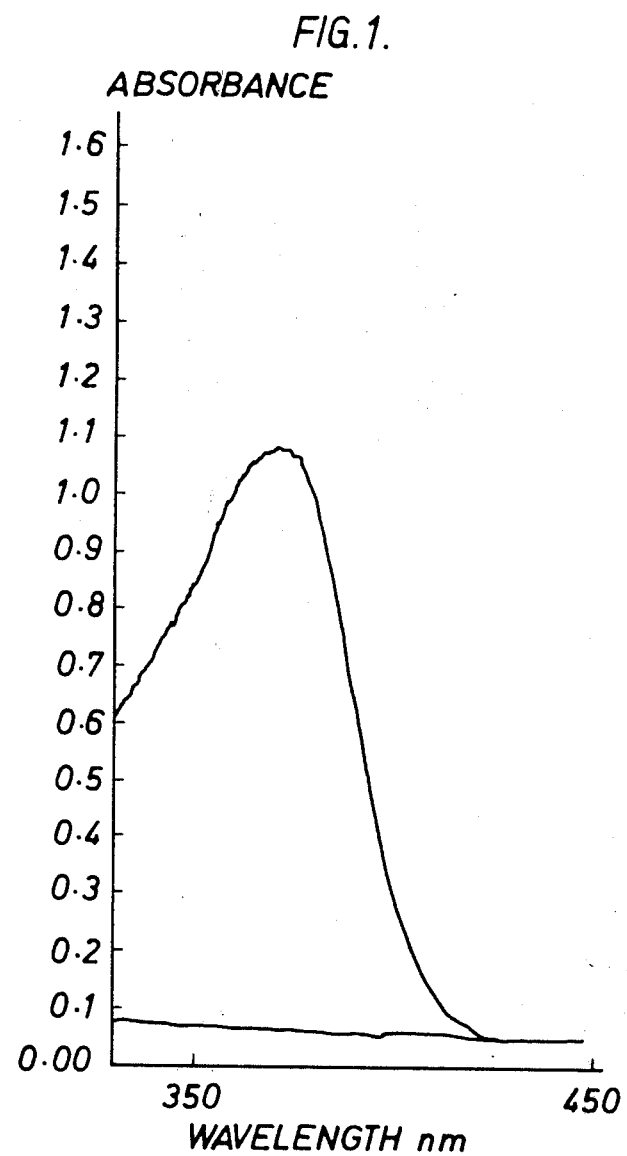
Figure 2:
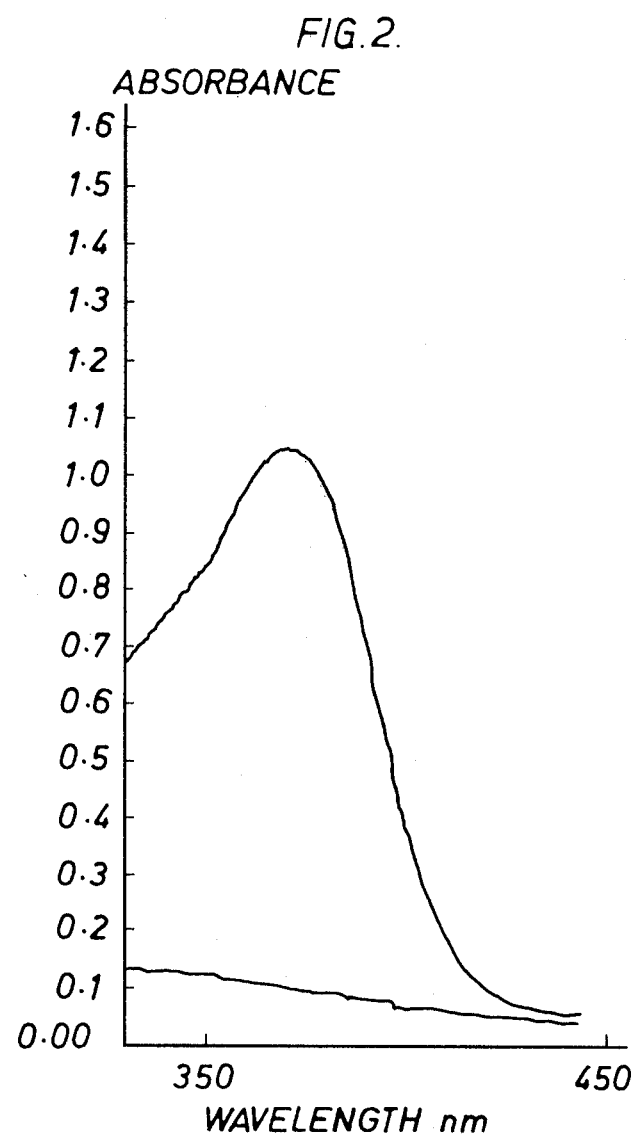

United States Patent [19]

Postle

[11] 4,359,523
[45] Nov. 16, 1982

[54] PHOTOGRAPHIC ELEMENT CONTAINING A UV-FILTER LAYER

[75] Inventor: Stephen R. Postle, Brentwood, England

[73] Assignee: Ciba-Geigy AG, Basel, Switzerland

[21] Appl. No.: 291,697

[22] Filed: Aug. 10, 1981

[30] Foreign Application Priority Data

Aug. 29, 1980 [GB] United Kingdom ............... 8028071

[51] Int. Cl.³ .............................................. G03C 1/78
[52] U.S. Cl. .................... 430/512; 430/931; 523/135
[58] Field of Search .................. 430/512, 931, 4; 350/1.1; 523/135

[56] References Cited

U.S. PATENT DOCUMENTS 4,052,216 10/1977 Sobel et al. ................. 430/931
4,245,018 1/1981 Hara et al. ................. 430/512
4,309,500 1/1982 Shishido ................. 430/515

Primary Examiner—Jack P. Brammer
Attorney, Agent, or Firm—Joseph G. Kolodny

[57] ABSTRACT

Light-sensitive photographic material which contains a non-light sensitive uv-filter layer comprising a compound of the general formula

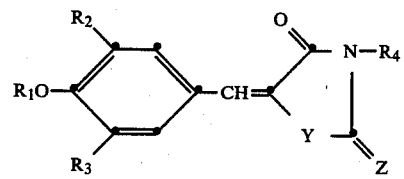

wherein $R_1$ is alkyl or a group of the formula

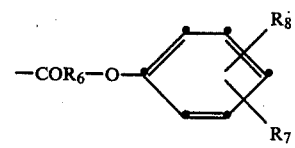

wherein $R_6$ is alkylene and $R_7$ and $R_8$ are each alkyl or one of $R_7$ and $R_8$ can be hydrogen, $R_2$ and $R_3$ are each hydrogen or alkoxy, Z is oxygen or sulphur, Y is oxygen or sulphur or a group —$NR_5$—, wherein $R_5$ is hydrogen or optionally substituted alkyl, aryl or carboxyalkyl, and $R_4$ is hydrogen or optionally substituted alkyl, aryl or carboxyalkyl. These compounds exhibit a very sharp cut-off point at about 400 nm.

17 Claims, 2 Drawing Figures

PHOTOGRAPHIC ELEMENT CONTAINING A UV-FILTER LAYER

The present invention relates to light-sensitive photographic material which comprises an ultra-violet light (uv) absorbing layer.

It is common in photographic materials and in particular in colour photographic materials to provide an uv-absorbing layer to minimise the tendency of highlight areas which are not in fact blue from appearing blue in the final print. Various uv-absorbing compounds have been used for this purpose and their chief requirement is that they absorb all actinic light below 400 nm but have a very sharp cut-off point at about 400 nm. It has been found that a class of known compounds can be used in uv-absorbing layers because they have such a sharp cut-off point.

According to the present invention there is provided a light-sensitive photographic material which contains a non-light sensitive uv-filter layer comprising a compound of the general formula

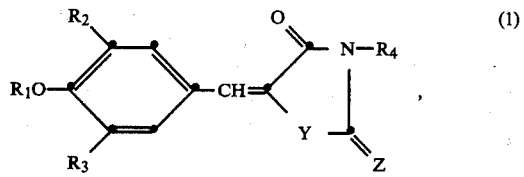

wherein $R_1$ is alkyl containing at least 10 carbon atoms or a group of the formula

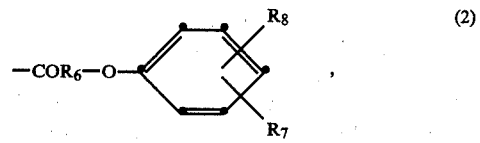

wherein $R_6$ is alkylene having from 1 to 5 carbon atoms and $R_7$ and $R_8$ are each alkyl having at least 8 carbon atoms, or one of $R_7$ and $R_8$ can be hydrogen.

$R_2$ and $R_3$ are each hydrogen or alkoxy having from 1 to 6 carbon atoms, Z is oxygen or sulphur, Y is oxygen or sulphur or a group $-NR_5-$, wherein $R_5$ is hydrogen or optionally substituted alkyl, aryl or carboxyalkyl, and $R_4$ is hydrogen or optionally substituted alkyl, aryl or carboxyalkyl.

Another object of the present invention is a process for the manufacture of the inventive photographic material.

Suitable alkyl groups $R_1$ in compounds of formula (1) contain at least 10 carbon atoms. Preferably, these alkyl groups contain 10 to 30 carbon atoms. Mostly preferred are alkyl groups having 12 to 26 carbon atoms. Suitable alkyl radicals are dodecyl, tetradecyl, pentadecyl, hexadecyl, octadecyl, eicosyl, docosyl, tetracosyl and hexacosyl as well as isomers thereof. Pentadecyl and octadecyl radicals are especially preferred. Further, $R_1$ denotes a group of the formula

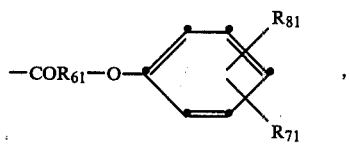

In this formula, $R_6$ is an alkylene linking group having from 1 to 5, preferably 1 to 3 carbon atoms. $R_7$ and $R_8$ are independently from each other hydrogen or alkyl having at least 8 carbon atoms. Preferably, $R_7$ and $R_8$ are totalling 10 to 15 carbon atoms. Thus it is possible, that $R_7$ and $R_8$ are each alkyl having together at least 8 carbon atoms, or $R_7$ or $R_8$ is hydrogen and $R_8$ or $R_7$ is alkyl having at least 8 carbon atoms. Species of suitable alkyl groups are listed above.

Groups of the formula (2) are oil-solubilising groups and are often used to confer oil-solubility to colour couplers.

Z in the compounds of the formula (1) is oxygen or, preferably, sulphur.

Y is oxygen, sulphur or a group of the formula $-NR_5-$, wherein $R_5$ is hydrogen, methyl, ethyl, propyl or butyl, optionally substituted by methoxy, aryl such as naphthyl or phenyl, or carboxyalkyl wherein the alkylmoiety contains 1 to 4, preferably 1 or 2 carbon atoms. Preferably, Y is oxygen, sulphur or imino and most preferably, Y is oxygen or sulphur.

$R_4$ is hydrogen or alkyl having 1 to 4 carbon atoms such as methyl, ethyl, propyl, butyl or t-butyl. These radicals are optionally substituted by methoxy or ethoxy. Preferably, the alkyl groups $R_4$ are unsubstituted and represent methyl or ethyl. Hydrogen is a further preferred meaning of $R_4$. $R_4$ denotes further aryl such as naphthyl or, preferably, phenyl. These aryl groups are optionally substituted by methoxy, ethoxy, chlorine or bromine. $R_4$ is also carboxyalkyl, wherein the alkyl moiety contains 1 to 4 carbon atoms. Preferred meanings of $R_4$ are hydrogen, methyl or ethyl.

$R_2$ and $R_3$ are independently of each other hydrogen or alkoxy having 1 to 6 carbon atoms such as methoxy, ethoxy, propoxy, butoxy, t-butoxy, pentoxy and hexoxy. Preferably, $R_2$ is hydrogen and $R_3$ is hydrogen or methoxy.

Preferred light-sensitive photographic materials comprise a compound of the formula (1), wherein $R_1$ is alkoxy having 12 to 26 carbon atoms or a group of the formula

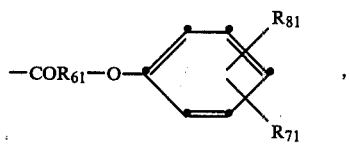

wherein $R_{61}$ is alkylene having 1 to 3 carbon atoms, $R_{71}$ and $R_{81}$ having 10 to 15 carbon atoms or one of $R_{71}$ and $R_{81}$ can be hydrogen.

In suitable light-sensitive materials, Y is oxygen, sulphur or imino and in more preferred materials, Y is oxygen or sulphur.

In further preferred materials, Z is sulphur.

Interesting materials comprise a compound of the formula (1), wherein $R_4$ is hydrogen, alkyl having 1 to 4 carbon atoms optionally substituted by methoxy or ethoxy, phenyl optionally substituted by methoxy, ethoxy, chlorine or bromine, or carboxylalkyl having 2 to 5 carbon atoms.

Preferred is a material, wherein $R_4$ is hydrogen or alkyl having 1 to 4 carbon atoms, and more preferably $R_4$ in the compound of the formula (1) is hydrogen, methyl or ethyl.

Suitable materials comprise a compound of the formula (1), wherein $R_3$ is hydrogen, methoxy, ethoxy, butoxy, pentoxy or hexoxy.

In more suitable materials, $R_3$ in the compounds of the formula (1) is hydrogen or methoxy.

In further preferred materials, $R_2$ in the compounds of the formula (1) is hydrogen.

Mostly preferred is a material, wherein in the compound of the formula (1), $R_1$ is alkyl having 12 to 26 carbon atoms or a group of the formula (3), Y is oxygen or sulphur, Z is sulphur, $R_4$ is hydrogen, methyl or ethyl, $R_3$ is hydrogen or methoxy and $R_2$ is hydrogen.

Preferably the photographic material comprises in the supercoat layer the compounds of formula (1). Most preferably the supercoat layer is a non-light sensitive gelatin layer and the compounds of formula (1) have been added to the aqueous gelatin coating solution from which the supercoat is prepared either as an aqueous solution or as an organic solvent solution wherein the organic solvent is water-miscible. Alternatively the compounds of formula (1) may be present in the supercoat layer as an oil dispersion or as a solid dispersion.

The coating weight of the compounds of formula (1) in the uv-filter layer is usually within the range of 1–10 mg/dm$^2$.

The compounds of formula (1) when formulated in a uv-filter layer absorb all uv-light up to and including 400 nm light, but their absorption does not extend appreciably into the visible regions of the spectrum. Thus the compounds are either colourless or very pale yellow. They have no appreciable visible density at the coating weight usually employed for filter layers.

The compounds of formula (1) are known benzylidene dyes. They may be prepared by reaction of the appropriate methylene compound with the appropriate aldehyde compound.

PREPARATION 1

3-Methylthiohydantoin (0.65 g, $5 \times 10^{-3}$ mol) and 4-octadecyloxy benzaldehyde (1.87 g, $5 \times 10^{-3}$ mol) are heated under reflux in 2-methoxyethanol (5 ml) with methylamine (2 drops) for 60 minutes. Solvent is evaporated at reduced pressure, and the solid remaining crystallised from ether to give a pale yellow solid, m.p. 131°–132° C., of formula

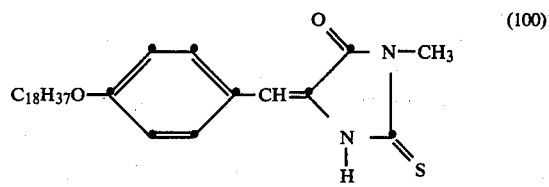
(100)

The uv-spectrum of this dye in acetonitrile solution is shown on FIG. 1 ($\lambda$max 371 nm, $\epsilon$max $1.68 \times 10^4$). It is substantially the same in an oil emulsion coated in gelatin on clear base.

PREPARATION 2

3-Ethyloxarhodanine (0.73 g, $5 \times 10^{-3}$ mol) and 4,4'-3''-pentadecylphenoxy)butyryloxy benzaldehyde (2.47 g, $5 \times 10^3$ mol) are heated in 2-methoxy ethanol (5 ml) under reflux for 2 minutes in the presence of triethylamine (2 drops). Solvent is then removed and the viscous oil remaining purified by column chromatography (1:1 ether/light petroleum/silica) to give a colourless oil of formula

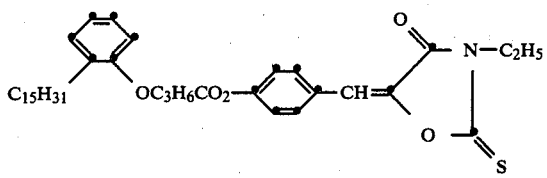

The uv-spectrum of this dye, measured in ethanol solution, is shown in FIG. II ($\lambda$max 371 nm, $\epsilon$max $1.32 \times 10^4$). It is substantially unaltered in oil emulsions coated in gelatin on clear base.

Other useful compounds of this class are:

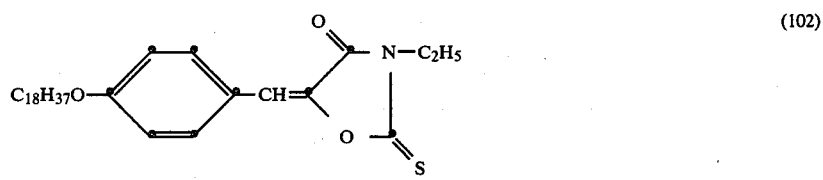
(102)

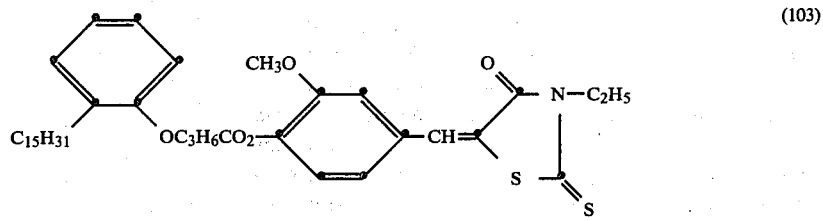
(103)

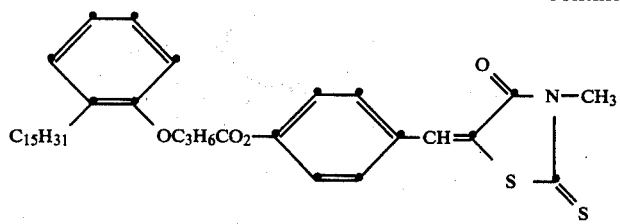

(104)

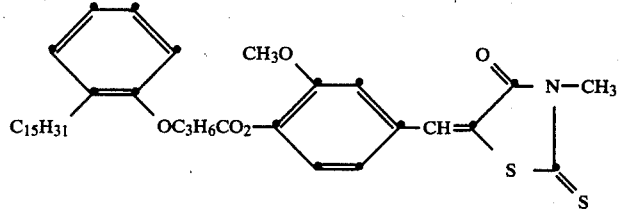

(105)

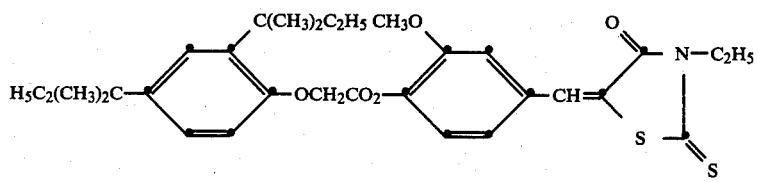

(106)

EXAMPLE

A photographic silver halide material having a uv-absorbing layer is prepared as follows:

A silver iodobromide emulsion containing 2% iodide to 98% bromide is prepared. A portion of this emulsion which contains 70 mg gelatin and 70 mg silver has dispersed in it 30 mg of the yellow colour coupler of formula

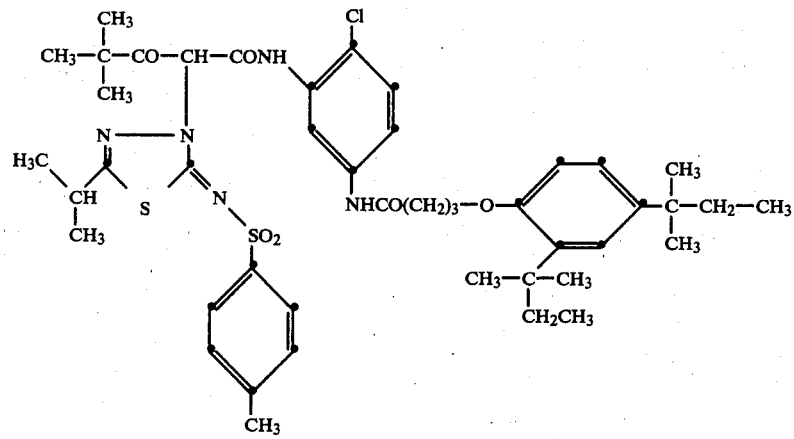

5γ{-[2,4-Bis(1,1-dimethylpropyl)-phenoxy]-butyramido}-2-chloro-α-[5-isopropyl-2-(4-tolylsulphonylimino)-Δ⁴-1,3,4-thiadiazolin-3-yl]-α-pivaloylacetanilide in tri-isopropyl phenyl phosphate. The resulting emulsion is coated on to 1 dm² of subbed polyester support and the coating dried.

On this silver halide emulsion layer is coated a non-stress layer which comprises compound (100) as an uv-absorber. This layer is prepared as follows.

The following solution is prepared:

| Compound (100) | 1 g |

| -continued | |
|---|---|
| Di-n-butyl phthalate (DBP) | 1 g |
| Ethyl acetate | 1 g |
| 10% gelatin solution | 8 g |
| 10% anionic wetting agent | 2 ml |
| Distilled water | 2 ml | by dissolving compound (100) in the DBP and ethyl acetate on a hot plate. Then the gelatin solution to (107)

which the distilled water and wetting agent has been added is heated to 50° C. The solution of compound (100) is added to the gelatin solution and mixed in an ultrasonic mixer for two minutes.

A gelatin non-stress layer is prepared containing:

| Gelatin | 0.9 g |
|---|---|
| Distilled water | 22.5 g |
| Dispersion of compound (100) as just prepared | 1.73 g |
| 10% wetting agent | 0.7 ml |

0.62 ml of this solution is coated on to the 1 dm² polyester support coated with the silver halide emulsion layer and the coating dried. The gelatin coating weight of the dried non-stress layer is 23.8 mg per 1 dm² and the coating weight of compound (100) is 2.8 mg per 1 dm².

A strip of this material (strip A) is taken and exposed with a standard step wedge to a tungsten halogen light source, and processed at 37.8° C. in the following solutions:

| 1. Colour developing developer bath: | 3¼ minutes |
|---|---|
| Potassium carbonate | 37.5 g |
| Sodium metabisulphite (anhydrous) | 4.25 g |
| Potassium iodide | 2.0 mg |
| Sodium bromide | 1.3 g |
| Hydroxylamine sulphate | 2.0 g |
| 4-(N—ethyl-N—β-hydroxyethylamino)-2-methylaniline sulphate | 4.75 g |
| Water to make up to | 1 liter. |
| 2. Bleaching bleaching bath: | 6½ minutes |
| Ammonium bromide | 150 g |
| Ammonium salt of the iron-III-complex of ethylenediamine tetra-acetic acid | 175 ml |
| Acetic acid (glacial acetic acid) | 10.5 ml |
| Sodium nitrate | 35 g |
| Water to make up to | 1 liter. |
| 3. Washing | 3¼ minutes |
| 4. Fixing fixing bath: | 6½ minutes |
| Ammonium thiosulphate (50% aqueous) | 16.2 ml |
| Diethylenetriaminepenta-acetic acid | 1.25 g |
| Sodium metabisulphite (anhydrous) | 12.4 g |
| Sodium hydroxide | 2.4 g |
| Water to make up to | 1 liter. |
| 5. Washing | 3¼ minutes |
| 6. Stabilising stabiliser bath: | |
| Formaldehyde (35% aqueous solution) | 5.0 ml |
| Water to make up to | 1 liter. |

A yellow image is obtained showing that the film is sensitive to blue light. Another strip (A) is exposed briefly to a mercury vapour lamp, with a standard step wedge. After processing as above no image is obtained.

This shows that compound (100) acts as an uv-absorber during the exposure of the photographic material but is also present in the processed photographic material and thus would help to preserve the yellow dye image from deterioration caused by uv-light if the processed strip are to be used as a negative in subsequent exposing and printing operations.

A strip of material is then taken by coating the silver halide emulsion layer alone, without the uv-filter layer (strip B). Separate pieces of this are exposed to both the tungsten halogen light source and to the mercury vapour lamp. In each case an image is obtained after processing. This further demonstrates the uv-absorbing nature of the compounds of this invention.

I claim:

1. A light-sensitive photographic element which contains a silver halide emulsion layer and non-light sensitive uv-filter layer comprising a compound of the formula

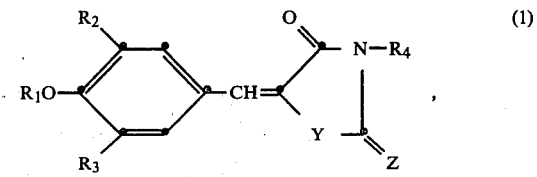

wherein $R_1$ is alkyl containing at least 10 carbon atoms or a group of the formula

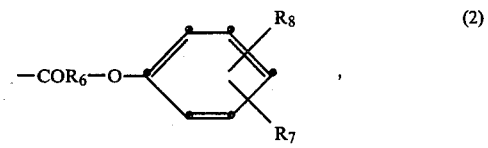

wherein $R_6$ is alkylene having from 1 to 5 carbon atoms and $R_7$ and $R_8$ are each alkyl having at least 8 carbon atoms, or one of $R_7$ and $R_8$ can be hydrogen, $R_2$ and $R_3$ are each hydrogen or alkoxy having from 1 to 6 carbon atoms, Z is oxygen or sulphur, Y is oxygen or sulphur or a group —$NR_5$—, wherein $R_5$ is hydrogen or optionally substituted alkyl, aryl or carboxyalkyl, and $R_4$ is hydrogen or optionally substituted alkyl, aryl or carboxyalkyl.

2. A light sensitive element according to claim 1, wherein $R_1$ is alkyl having 12 to 26 carbon atoms or a group of the formula

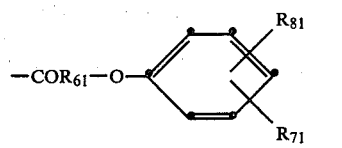

wherein $R_{61}$ is alkylene having 1 to 3 carbon atoms, $R_{71}$ and $R_{81}$ having 10 to 15 carbon atoms or one of $R_{71}$ and $R_{81}$ can be hydrogen.

3. A light-sensitive element according to claim 1, wherein Y is —O—, —S— or —NH—.

4. A light-sensitive element according to claim 3, wherein Y is —O— or —S—.

5. A light-sensitive element according to claim 1, wherein Z is sulphur.

6. A light-sensitive element according to claim 1, wherein $R_4$ is hydrogen, alkyl having 1 to 4 carbon atoms optionally substituted by methoxy or ethoxy, phenyl optionally substituted by methoxy, ethoxy, chlorine or bromine, or carboxyalkyl having 2 to 5 carbon atoms.

7. A light-sensitive element according to claim 6, wherein $R_4$ is hydrogen or alkyl having 1 to 4 carbon atoms.

8. A light-sensitive element according to claim 7, wherein $R_4$ is hydrogen, methyl or ethyl.

9. A light-sensitive element according to claim 1, wherein $R_3$ is hydrogen, methoxy, ethoxy, butoxy, pentoxy or hexoxy.

10. A light-sensitive element according to claim 9, wherein $R_3$ is hydrogen or methoxy.

11. A light-sensitive element according to claim 1, wherein $R_2$ is hydrogen.

12. A light-sensitive element according to claim 1, wherein $R_1$ is alkyl having 12 to 26 carbon atoms or a group of the formula (3), Y is oxygen or sulphur, $R_4$ is hydrogen, methyl or ethyl, $R_3$ is hydrogen or methoxy and $R_2$ is hydrogen.

13. A light-sensitive photographic element according to claim 1 which is silver halide photosensitive material and the compound of formula (1) is present in a supercoat layer.

14. A light-sensitive photographic element according to claim 13 wherein the supercoat layer is a gelatin layer and the compound of formula (1) has been added to an aqueous gelatin supercoat coating solution either as an aqueous solution or as an organic solvent solution wherein the organic solvent is water-miscible.

15. A light sensitive photographic element according to claim 13 wherein the compound of formula (1) is present in the supercoat layer as an oil dispersion or as a solid dispersion.

16. A light-sensitive photographic element according to claim 1 wherein the compound of formula (1) is present within the range of 1–10 mg/dm².

17. A process for the manufacture of a light-sensitive photographic element according to claim 1, wherein a compound of the formula (1) is incorporated into a non-light sensitive layer of the element.

* * * * *